United States Patent [19]

Shubkin et al.

[11] Patent Number: 5,811,617
[45] Date of Patent: Sep. 22, 1998

[54] OLEFIN OLIGOMERIZATION PROCESS

[75] Inventors: Ronald L. Shubkin, Baton Rouge, La.; Tze-Chiang Chung; Ruidong Ding, both of State College, Pa.

[73] Assignee: Amoco Corporation, Chicago, Ill.

[21] Appl. No.: 572,278

[22] Filed: Dec. 13, 1995

[51] Int. Cl.6 .................................. C07C 2/04; C07C 2/26
[52] U.S. Cl. ..................... 585/511; 585/510; 585/517; 585/520; 585/521; 585/530
[58] Field of Search ..................... 585/510, 511, 585/517, 520, 521, 530; 502/150, 152, 153, 154, 159

[56] References Cited

U.S. PATENT DOCUMENTS

| | | | |
|---|---|---|---|
| 4,329,252 | 5/1982 | Gavens et al. | 526/129 |
| 4,734,472 | 3/1988 | Chung | 526/239 |
| 4,751,276 | 6/1988 | Chung | 526/158 |
| 5,288,677 | 2/1994 | Chung et al. | 502/152 |

*Primary Examiner*—Elizabeth D. Wood
*Attorney, Agent, or Firm*—James R. Henes; Stephen L. Hensley

[57] ABSTRACT

Alpha-olefin oligomer is prepared by contacting an alpha-olefin monomer which contains from about 8 to about 16 carbon atoms with a heterogeneous catalyst system formed from (i) a solid olefin polymer having a linear backbone and a plurality of pendant omega-hydroxyalkyl groups, and (ii) a boron trihalide, preferably $BF_3$. The catalyst system is stable and very reactive at relatively high temperatures, and the solid polymer of the catalyst system can be recovered and reused repeatedly in batch-type operations and can be used for long periods of time in continuous or semi-continuous operations.

17 Claims, No Drawings

OLEFIN OLIGOMERIZATION PROCESS

TECHNICAL FIELD

This invention relates generally to the preparation of alpha-olefin oligomers which are useful as synthetic lubricants and functional fluids, and more particularly to a novel catalytic process for conducting such oligomerizations.

BACKGROUND

Alpha-olefin oligomers and their use as synthetic lubricants are well-known. The oligomers are usually hydrogenated in order to improve their stability. Hydrogenated oligomers produced from 1-alkenes, especially linear 1-alkenes, having in the range of about 8 to about 14 carbon atoms are generally deemed most suitable for use as synthetic lubricants and fluids. Hydrogenated oligomer oils with viscosities of about 2–10 cSt at 100° C. are typically used for general lubricating oil applications. These materials are, in general, mixtures of different percentages of dimer, trimer, tetramer, pentamer and, in the case of the higher viscosity products in this range, higher oligomers as well. For some lubricant applications, hydrogenated oligomers with still higher viscosities are desired.

While various types of alpha-olefin oligomerization catalysts have been disclosed, catalysts based on boron trifluoride have proven most useful. Patent literature on $BF_3$-based alpha-olefin oligomerization includes U.S. Pat. Nos. 2,806,072; 3,149,178; 3,382,291; 3,769,363; 3,997,621; 4,172,855; 4,218,330; 4,436,947; 4,982,026; 5,068,487; 5,191,140; 5,396,013; and 5,420,373. As indicated in these disclosures, a suitable promoter is used with the $BF_3$ to render it suitably effective for effecting the oligomerization.

Although the boron trifluoride-based catalyst systems exemplified by the above patents are effective, they are not without drawbacks or deficiencies. Chief among these are the problems of recovery and disposal of the catalyst residues. See for example U.S. Pat. Nos. 4,213,001; 4,263,467; 4,308,414; 4,384,162; 4,394,296; 4,433,197; 4,454,366; and 4,981,578 which describe various ways of coping with these problems.

U.S. Pat. No. 5,288,677 discloses immobilized Lewis acid catalysts and their use as catalysts for the polymerization of isobutylene, mixed butenes and copolymerization of monomers including 1-butene, ethylene and 1-hexene. One of the catalysts used for polymerization of isobutylene is hydroxylated polybutene-1 copolymer which has been reacted with $BF_3$ in a manner to form a sigma ($\sigma$) bond between the boron and oxygen atoms. For ease of description this copolymer is depicted in simplified form in the patent as PB-O-$BF_2$ ("PB" referring to polybutene). Additional experiments have been conducted using PP-O-$BF_2$ catalyst systems, such as:

PP—O—$BF_2$/n-BuOH;
PP—O—$BF_2$/n-BuOH/$CH_2Cl_2$;
PP—O—$BF_2$/HCl;
PP—O—$BF_2$/HCl/$CH_2Cl_2$;
PP—O—$BF_2$/HCl;
PP—O—$BF_2$/t-BuCl; and
PP—O—$BF_2$/$BF_3$ (gaseous $BF_3$)

where "PP" refers to polypropylene, n-BuOH is n-butanol, $CH_2Cl_2$ is methylene chloride, and t-BuCl is tertiary butyl chloride, and where the $BF_3$ was in gaseous form. This work has shown that all of these additional systems show good reactivity in polymerizing isobutylene and styrene. Unfortunately, all of these systems showed no reactivity to 1-octene.

SUMMARY OF THE INVENTION

This invention in one of its embodiments provides a new catalytic process for producing 1-olefin oligomers which utilizes a stable catalyst system that is very reactive at relatively high temperatures, and that is readily recoverable and reusable in further oligomerization reactions. In accordance with this embodiment, a 1-olefin having in the range of about 8 to about 16, and preferably about 8 to about 12 carbon atoms, or a mixture of two or more such 1-olefins, is oligomerized by contact with an catalyst system formed from (i) a solid olefin polymer having a linear backbone and a plurality of pendant omega-hydroxyalkyl groups, and (ii) a boron trihalide, most preferably boron trifluoride. Studies have indicated that the components (i) and (ii) form a complex under ordinary ambient temperature conditions.

The oligomerization process of this invention is very easy to carry out. All that is required is to introduce the boron trihalide into a heterogeneous mixture of the liquid 1-olefin to be oligomerized and the solid olefin polymer having pendant omega-hydroxyalkyl groups. Oligomerization proceeds readily in short reaction periods and at convenient reaction temperatures, including room temperature.

One important advantage of this catalyst system is that the solid polymer of the catalyst system can be recovered and reused repeatedly in batch-type operations and can be used for long periods of time in continuous or semi-continuous operations. Thus in a batch-type process, the solid catalyst material can be readily separated from the product by filtration or like physical separation procedure, and used in ensuing operations. In continuous and semi-continuous operations the solid polymer of the catalyst system can be used as a bed through which the olefin is passed. In all cases, all that is required is to periodically introduce boron trihalide at intervals sufficient to maintain the catalytic activity of the catalyst system.

Another feature of this invention is the fact that by utilizing appropriate combinations of reaction time and temperature, oligomer product mixtures having different proportions of dimers, trimers, tetramers, etc., can be formed. For example, by increasing the temperature products having higher proportions of dimer and trimer and smaller proportions of tetramer and higher oligomers can be formed. Similarly, by keeping the temperature relatively low and increasing the reaction period the proportion of dimer in the product mixture can be decreased.

The above and other embodiments and features of this invention will become still further apparent from the ensuing description and appended claims.

FURTHER DESCRIPTION

Olefins for Oligomerization

The olefins used in making the oligomers are predominately (at least 50 mole %) $C_8$–$C_{16}$ and preferably predominately $C_8$–$C_{12}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-octene, 1-nonene, 1-decene, 1-undecene, 1-dodecene, 1-tridecene, 1-tetradecene, 1-pentadecene, 1-hexadecene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1- octene, 7,7-dimethyl-1-octene,8-methyl-1-nonene, and like 1-olefins can also be used especially when used together with linear 1-olefins. The more preferred olefins are linear alpha-olefin monomers containing about 8–14 carbon atoms. The most preferred 1-olefin monomers are 1-octene, 1-decene, 1-dodecene and mixtures of any two or all three of these.

Minor amounts of up to about 50, and usually less than 25 mole % of internal and/or vinylidene olefins can be present in the olefin monomers.

Olefin Polymer with Pendant Omega-Hydroxyalkyl Groups

The olefin polymer having pendant omega-hydroxyalkyl groups can be prepared in a two-stage operation. In the first stage a polymer having hydrocarbyl-borohydrocarbyl groups depending from the backbone is formed. This involves either homopolymerizing or copolymerizing a hydrocarbyl borane monomer having an omega-alkenyl group (e.g., B-(5-hexen-1-yl)-9-BBN, B-(7-octen-1-yl)-9-BBN, etc.) as described for example in U.S. Pat. Nos. 4,734,472 and 4,751,276. The polymerization is effected using a suitable Ziegler-Natta catalyst system such as $TiCl_3AA/AlEt_2Cl$ (where "AA" means alumina activated). Procedures for producing the hydrocarbylborane monomers are also described in these two patents. When forming the copolymers, the hydrocarbyl borane having an omega-alkenyl group is copolymerized with at least one straight chain 1-olefin, preferably a straight chain 1-olefin having 3–10 (more preferably 3–6) carbon atoms or a mixture of any two or more of these, most preferably propylene. The copolymers formed in this first stage may contain from 0.1 to 99.9 mol % of units derived from the hydrocarbyl borane monomer and from 99.9 to 0.1 mol % of units derived from the straight chain 1-olefin(s). Preferred copolymers have from about 1 to about 15 mol % of units derived from the hydrocarbyl borane monomer and from about 99 to about 85 mol % of units derived from the straight chain 1-olefin(s).

In the second stage the hydrocarbylborane-substituted polymer formed in the first stage is reacted with an inorganic base and a peroxide, preferably sodium hydroxide and hydrogen peroxide, to form the olefin polymer having pendant omega-hydroxyalkyl groups. Once again U.S. Pat. Nos. 4,734,472 and 4,751,276 provide a detailed description of this synthesis procedure.

Suitable olefin polymers having pendant omega-hydroxyalkyl groups comprise poly(1-alken-$\bar{\omega}$-ol) polymers in which the 1-alken-$\bar{\omega}$-ol units contain 6 to about 12 carbon atoms each, and poly(1-alkene-co-1-alken-$\bar{\omega}$-ol) polymers in which the alkene units contain 3 to about 10 carbon atoms each and the 1-alken-$\bar{\omega}$-ol units contain 6 to about 12 carbon atoms each. The homopolymers are typified by poly(1-hexen-6-ol) and poly(1-octen-8-ol). The copolymers include poly(1-butene-co-1-alken-$\bar{\omega}$-ol) polymers, such as poly(1-butene-co-1-hexen-6-ol) and poly(1-butene-co-1-octen-8-ol); poly(1-pentene-co-1-alken-$\bar{\omega}$-ol) polymers, such as poly(1-pentene-co-1-hexen-6-ol) and poly(1-pentene-co-1-hepten-7-ol); and poly(1-hexene-co-1-alken-$\bar{\omega}$-ol) polymers, such as poly(1-hexene-co-1-hexen-6-ol) and poly(1-hexene-co-1-decen-10-ol). Particularly preferred olefin polymers having pendant omega-hydroxyalkyl groups are poly(propylene-co-1-alken-$\bar{\omega}$-ol) polymers, such as poly (propylene-co-1-hexen-6-ol), poly(propylene-co-1-hepten-7-ol), poly(propylene-co-1-octen-8-ol), poly(propylene-co-1-nonen-9-ol), 9-ol), and poly(propylene-co-1-decen-10-ol). These propylene-derived copolymers are when suitably prepared have crystallinity and brush-like molecular structures with the hydroxyl groups at the ends of flexible side chains. Note in this connection, T. C. Chung, *Polymer News*, 1993, Volume 18, pages 38–43 and *Chemtech*, 1991, Volume 21, pages 496–499. Thus they are capable of forming highly active catalytic complexes with the boron halide. Poly (propylene-co-1-hexen-6-ol) is a particularly preferred hydroxyalkyl olefin polymer catalyst component for use in the practice of this invention.

Oligomerization Reaction

In conducting the oligomerization process of this invention, oligomerization is effected by contacting the monomer(s) with a catalytic amount of the catalyst system. Typical catalytic amounts fall in the range of about 1% to about 20% of the weight of the monomer to be oligomerized. Preferably the catalyst system is used in the range of about 5% to about 10% of the weight of the 1-olefin monomer. Oligomerization temperatures are typically in the range of about 0° to about 80° C., and preferably are in the range of about 20° to about 60° C. Thus in conducting the oligomerization reactions of this invention at least a substantial portion of each individual reaction (e.g., at least for one-half of the total reaction period) the oligomerization reaction is performed at one or more temperatures in the foregoing ranges. To ensure intimate contact between the liquid oligomer and heterogeneous catalyst system, the reaction mixture can be agitated during the reaction, or the liquid phase can be passed through a bed of the catalyst system. Reaction times will vary depending on the type of product desired and reaction conditions used. Generally speaking reaction times will fall in the range of about 0.25 to about 3 hours. However departures from this range are permissible whenever deemed necessary or desirable, and are within the scope of this invention.

Conventional protic catalyst promoters are not required, but can be used if desired. Among promoters that can be used are water, carboxylic acids, mineral acids, alcohols, phenols, carboxylic acid esters and anhydrides, ketones, aldehydes, hydroxy ketones, hydroxy aldehydes, alcohol alkoxylates, and mixtures of any two or more of the foregoing. If and when used, the amount of such promoter is typically from about 0.001 to about 0.04 moles per mole of 1-olefin monomer(s). The promoter can be mixed with the olefin feed or the promoter can be charged separately to the reactor, either entirely at the outset or portionwise as the oligomerization proceeds.

In conducting the oligomerization process of this invention the 1-olefin or mixture of 1-olefins, boron trihalide, and polymer having pendant omega-hydroxyalkyl groups can be charged to the reactor in any suitable sequence. Preferably, however, the boron trihalide is introduced directly into a heterogeneous mixture of the 1-olefin and the solid polymer having pendant omega-hydroxyalkyl groups. As noted above, boron trifluoride is the preferred boron trihalide for use in forming the catalyst system.

The oligomerization reaction is typically conducted at about atmospheric pressure, but super-atmospheric pressures can be used, if desired. Normally it is unnecessary to exceed pressures of about 100 psig. If it is desired to monitor the progress of the reaction, samples of the oligomerization mixtures can be taken at suitable periods during the course of the reaction and subjected to gas chromatographic (GC) analysis. The reaction can be conducted in a single stirred reactor or in a series of reactors. Alternatively, the reactor may contain a bed of the catalyst through which the liquid phase is continuously circulated in a closed loop.

To terminate the oligomerization reaction, the reaction mixture is simply separated from the heterogeneous catalyst for further processing such as distillation and/or hydrogenation. Unreacted olefin can be recovered and recycled.

As indicated above, because a heterogeneous catalyst is used in the process, the alpha-olefin oligomers can be in a series of two or more separate oligomerization reactions wherein the same solid polymer component of the catalyst is used over and over again. Thus in one of its embodiments this invention provides a process which comprises:

a) conducting a first or initial reaction of a series of separate oligomerization reactions by contacting at least one oligomerizable 1-olefin having in the range of about 8 to about 16 carbon atoms per molecule with a catalyst system formed from (i) a solid olefin polymer having a linear backbone and a plurality of pendant omega-hydroxyalkyl groups, and (ii) a boron trihalide, whereby the oligomerization results in a reaction mixture comprising a liquid alpha-olefin oligomer phase and a solids phase comprising solid olefin polymer catalyst residue;

b) separating the liquid phase and said solids phase from each other; and c) conducting another such reaction by contacting least one oligomerizable 1-olefin having in the range of about 8 to about 16 carbon atoms per molecule with a catalyst system formed from (i) the separated solids phase from the preceding reaction and (ii) a fresh charge of boron trihalide.

Thus a series of 5, 10, 15 or more successive separate oligomerization reactions can be performed in which after the end of each reaction the liquid phase and the solids phase are separated from each other, and the solids phase is used together with a fresh charge of boron trihalide (preferably boron trifluoride) and a fresh charge of an oligomerizable 1-olefin in conducting the next oligomerization reaction of that series of reactions. The 1-olefin can of course be varied from one run to the next.

Solvents or reaction diluents such as suitable paraffinic or naphthenic oils or paraffinic, cycloparaffinic or aromatic hydrocarbons such as hexane, heptane, octane, decane, cyclohexane, toluene, xylene, etc., can be employed if desired. Excess unreacted olefin can also serve as a diluent. Whenever deemed necessary or desirable, the oligomer can be recovered from the liquid phase in which it is formed by conventional procedures such as distillation.

In order to demonstrate the beneficial results achievable by the practice of this invention, an extended series of batch-type oligomerizations of 1-octene was carried out using a preferred catalyst system of this invention, namely a system formed from poly(propylene-co-1-hexen-6-ol) ("PP—OH") and boron trifluoride. A typical procedure for producing PP—OH involves:

(a) forming B-(5-hexen-1-yl)-9-borobicyclo[3.3.1]nonane ("hexenyl-9-BBN"), (b) copolymerizing the hexenyl-9-BBN with propylene to form poly(propylene-co-1-hexen-6-yl-9-BBN), and (c) oxidizing this boron-containing polyolefin polymer to PP—OH by use of sodium hydroxide and hydrogen peroxide.

Although full details for conducting such procedures are published in patents and technical journals, illustrative procedures are given below. It is to be noted that the copolymerization described in Example 2 below is performed using a new continuous process that gives superior results as compared to prior batch-type polymerizations. Synthesis details and oligomerization procedures and results are illustrated by the following examples.

EXAMPLE 1

Preparation of Hexenyl-9-BBN

A dry 2-liter flask is equipped with a magnetic stirring bar and a connecting tube leading to a nitrogen source. The flask is thoroughly flushed with nitrogen before the injection inlet is capped with a rubber serum stopple. A slight positive pressure of nitrogen is maintained in the flask thereafter. The flask is charged via syringe with 190 mL (1.6 mol) of 1,5-hexadiene. To the stirred diene solution is then added (via syringe) 800 mL of a 0.5 molar 9-BBN-THF solution. The reaction is effected with constant stirring at room temperature. After a period of 3 hours, excess 1,5-hexadiene and THF solvent are stripped by distillation at reduced pressure. Pure hexenyl-9-BBN is obtained at 130° C. and 10 $\mu$m.

EXAMPLE 2

Copolymerization of Propylene and Hexenyl-9-BBN in a Continuous Reaction

In a typical operation, 15.477 g of hexenyl-9-BBN and 200 mL of hexane are placed in an argon filled Parr stirred pressure reactor and sealed. Then 12 g of propylene is added under $N_2$ pressure. A slurry of 1.027 g of $TiCl_3$ and 4.705 g of $AlEt_2Cl$ in 80 mL of toluene are then added under $N_2$ pressure to catalyze the copolymerization. Additional propylene is added at 30-minute intervals with 10, 8, 6 and 5 g of propylene added, respectively. After the last monomer charge, the reaction is run for an additional hour before terminating the reaction by injection of 100 mL of isopropyl alcohol. The reaction mixture is stirred for an additional ½ hour before venting the excess pressure and flushing the polymeric product with additional isopropyl alcohol. Some typical results for copolymerization of propylene and hexenyl-9-BBN using this continuous polymerization procedure are summarized in Table 1. The process produces copolymer with narrow compositional distribution and higher yield of borane monomer than previously reported procedures.

TABLE 1

| Run No. | Mol % Hexenyl-9-BN in Feed | Mol % Hexenyl-9-BBN in Copolymer | Reaction Time, hr | Yield, % |
| --- | --- | --- | --- | --- |
| 1 | 10 | 3.5 | 3 | 62 |
| 2 | 10 | 4.2 | 5 | 75 |
| 3 | 13 | 5.0 | 3 | 65 |
| 4 | 13 | 7.8 | 5 | 72 |

EXAMPLE 3

Oxidation of Propylene/Hexenyl-9-BBN Copolymer

Propylene/hexenyl-9-BBN copolymer and 700 mL of THF are placed in a 2-liter round bottom flask equipped with septum and stirrer. To the resultant non-homogeneous slurry is added dropwise a solution of 19 g of NaOH in 100 mL of degassed water. The flask is then cooled to 0° C. before slowly adding 87.6 g of degassed 30% $H_2O_2$ solution via a double tipped needle. The reaction mixture is allowed to slowly come to room temperature before heating up to 55° C. for 6 hours. The PP—OH polymer, poly(propylene-co-1-hexen-6-ol, is then precipitated in water, squeeze dried, and placed in a slurry 500 mL of methanol. After 3 hours of vigorous stirring, approximately 75 mL of MeOH is distilled off under $N_2$ to remove boric acid-methanol azeotrope. The polymer is again precipitated in water, squeeze dried, washed with acetone, and dried under high vacuum at 45° C. Typical properties of the PP—OH polymer formed in this manner and of polypropylene homopolymer made in by the same polymerization method (Run No. 5) are summarized in Table 2. The PP—OH polymers of Run Nos. 6 and 7 of Table 2 were produced from the hexenyl-9-BBN polymers of Run Nos. 1 and 3 of Table 1, respectively. Molecular weights were determined by intrinsic viscosity as measured in a cone/plate viscometer at 135° C. in decalin solution.

TABLE 2

| Run No. | Mol % OH in Polymer | Melting Pt., °C. | Heat of Fusion, J/g | Intrinsic Viscosity | Mυ, g/mol |
|---|---|---|---|---|---|
| 5 | none | 163 | 62.5 | 2.07 | 230,000 |
| 6 | 3.5 | 161 | 54.1 | 1.78 | 183,000 |
| 7 | 5.0 | 158 | 44.6 | 1.71 | 174,000 |

Without desiring to be bound by theoretical considerations, the data in Table 2 indicate that the crystallinities, shown by melting point and heat of fusion, of the PP—OH polymers are not much different from that of the polypropylene homopolymer, which is therefore attributed to a tapered structure of the PP—OH polymer. Also, the functional groups on the side chains are concentrated at the end of the polymer chain indicating that the polypropylene units are in consecutive sequence to form crystalline phases.

EXAMPLE 4

Oligomerization of 1-Octene with PP—OH/Boron Trifluoride Catalyst

A series of 15 consecutive oligomerization reactions was conducted in which the same 0.7 gram sample of poly(propylene-co-1-hexen-6-ol) was recovered by filtration after each run and reused in the next run, a procedure that was repeated over and over again throughout the entire series. In each run the PP—OH copolymer and 20 mL of 1-octene were charged to an air-free flask and at the start of each run $BF_3$ was bubbled into the fresh mixture for 10 minutes while stirring the mixture. The slurry was then maintained under the selected reaction conditions for the desired reaction time. After each run the oligomer-containing reaction product was filtered to separate the PP—OH copolymer from the liquid oligomer-containing phase. The recovered PP—OH and a new 20 mL portion of 1-octene were charged to the flask for the next run. Table 3 summarizes the conditions used and the results obtained. Table 4 summarizes analytical data concerning the composition of some of the oligomers formed in these runs.

TABLE 3

| Run No. | Reaction Temp., °C. | Reaction Time hr. | Product Yield, g | Conversion, % |
|---|---|---|---|---|
| 1 | 20 | 1 | 7.28 | 50.9 |
| 2 | 20 | 1 | 7.31 | 51.1 |
| 3 | 20 | 1 | 7.51 | 52.5 |
| 4 | 20 | 1 | 7.40 | 51.7 |
| 5 | 20 | 1 | 7.14 | 49.9 |
| 6 | 20 | 1 | 7.59 | 53.0 |
| 7 | 20 | 1 | 7.32 | 51.1 |
| 8 | 20 | 1 | 7.28 | 50.9 |
| 9 | 20 | i | 7.38 | 51.6 |
| 10 | 20 | 1.5 | 9.60 | 67.1 |
| 11 | 20 | 1 | 7.24 | 50.6 |
| 12 | 40 | 1 | 9.98 | 69.8 |
| 13 | 60 | 1 | 13.35 | 93.3 |
| 14 | 60 | 0.5 | 6.91 | 48.3 |
| 15 | 20 | 1.5 | 10.40 | 72.7 |

TABLE 4

| Run No | Dimer, % | Trimer, % | Tetramer, % | Pentamer, % |
|---|---|---|---|---|
| 1 | 7.8 | 56.9 | 18.9 | 16.4 |
| 4 | 8.1 | 58.6 | 17.8 | 14.5 |
| 12 | 14.5 | 73.7 | 9.5 | 2.3 |
| 13 | 33.4 | 59.8 | 6.8 | trace |
| 14 | 35.4 | 64.0 | 0.6 | — |
| 15 | 5.8 | 66.0 | 17.1 | 11.1 |

The entire disclosure of each and every U.S. patent and each and every technical publication referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing alpha-olefin oligomer which comprises oligomerizing at least one oligomerizable 1-olefin having in the range of about 8 to about 16 carbon atoms per molecule by contacting said 1-olefin with a catalyst system formed from (i) a solid olefin polymer having a linear backbone and a plurality of pendant omega-hydroxyalkyl groups, and (ii) a boron trihalide, with the catalyst system at a level of about 1% to about 20% by weight of the oligomerizable 1-olefin and at a temperature of about 0° C. to about 80° C. and with at least 50 mole % of the at least one oligomerizable 1-olefin being at least one linear 1-olefin or a mixture thereof with at least one remotely branched 1-olefin.

2. A process according to claim 1 wherein said oligomerizable 1-olefin has about 8 to about 12 carbon atoms per molecule and said boron trihalide is boron trifluoride.

3. A process according to claim 1 wherein said solid olefin polymer is a poly(1-alkene-co-1-alken-$\bar{\omega}$-ol) polymer in which the alkene units contain 3 to about 10 carbon atoms each and the 1-alken-$\bar{\omega}$-ol units contain 6 to about 12 carbon atoms each.

4. A process according to claim 1 wherein said oligomerizable 1-olefin has about 8 to about 12 carbon atoms per molecule, wherein said solid olefin polymer is a poly(propylene-co-1-alken-$\bar{\omega}$-ol) polymer in which the 1-alken-$\omega$-ol units contain 6 to about 12 carbon atoms each, and wherein the boron trihalide is boron trifluoride.

5. A process according to claim 1 wherein said at least one oligomerizable 1-olefin is at least one linear 1-olefin.

6. A process of preparing alpha-olefin oligomer in a series of two or more separate oligomerization reactions which comprises:

a) conducting a first oligomerization reaction by contacting at least one oligomerizable 1-olefin having in the range of about 8 to about 16 carbon atoms per molecule with a catalyst system formed from (i) a solid olefin polymer having a linear backbone and a plurality of pendant omega-hydroxyalkyl groups, and (ii) a boron trihalide, whereby the oligomerization results in a reaction mixture comprising a liquid alpha-olefin oligomer phase and a solids phase comprising solid olefin polymer catalyst residue;

b) separating said liquid phase and said solids phase from each other; and c) conducting another said reaction by contacting at least one oligomerizable 1-olefin having in the range of about 8 to about 16 carbon atoms per molecule with a catalyst system formed from (i) said separated solids phase and (ii) a fresh charge of a boron trihalide;

wherein in each separate oligomerization reaction, the catalyst system is at a level of about 1% to about 20% by weight of the oligomerizable 1-olefin, the temperature is about 0° C. to about 80° C., and at least 50 mole % of the at least one oligomerizable 1-olefin is at least one linear 1-olefin or a mixture thereof with at least one remotely branched 1-olefin.

7. A process according to claim 6 wherein said series of separate oligomerization reactions comprises at least 5 successive separate oligomerization reactions in which after the end of each reaction said liquid phase and said solids phase are separated from each other and said solids phase is used together with a fresh charge of boron trihalide and a fresh charge of the aforesaid at least one oligomerizable 1-olefin having in the range of about 8 to about 16 carbon atoms per molecule in conducting the next oligomerization reaction.

8. A process according to claim 6 wherein in each said separate oligomerization reaction said oligomerizable 1-olefin has about 8 to about 12 carbon atoms per molecule and said boron trihalide is boron trifluoride.

9. A process according to claim 6 wherein said solid olefin polymer as charged to said first oligomerization reaction is a poly(1-alkene-co-1-alken-$\overline{\omega}$-ol) polymer in which the alkene units contain 3 to about 10 carbon atoms each and the 1-alken-$\overline{\omega}$-ol units contain 6 to about 12 carbon atoms each.

10. A process according to claim 6 wherein said oligomerizable 1-olefin in each of said two or more separate oligomerization reactions has about 8 to about 12 carbon atoms per molecule, wherein said solid olefin polymer as charged to said first oligomerization reaction is a poly (propylene-co-1-alken-$\overline{\omega}$-ol) polymer in which the 1-alken-$\overline{\omega}$-ol units contain 6 to about 12 carbon atoms each, and wherein the boron trihalide is boron trifluoride.

11. A process according to claim 6 wherein said solid olefin polymer as charged to said first oligomerization reaction is poly(propylene-co-(1-hexen-6-ol).

12. A process according to claim 10 wherein said poly (propylene-co-1-alken-$\overline{\omega}$-ol) polymer is poly(propylene-co-(1-hexen-6-ol).

13. A process according to claim 10 wherein said series of separate oligomerization reactions comprises at least 5 successive separate oligomerization reactions in which after the end of each reaction said liquid phase and said solids phase are separated from each other and said solids phase is used together with a fresh charge of boron trifluoride and a fresh charge of said oligomerizable 1-olefin in conducting the next oligomerization reaction.

14. A process according to claim 13 wherein at least 50 mole % of said at least one oligomerizable 1-olefin is at least one $C_8$–$C_{12}$ linear 1-olefin and wherein said poly(propylene-co-1-alken-$\overline{\omega}$-ol) polymer is poly(propylene-co-(1-hexen-6-ol).

15. A process according to claim 10 wherein said series of separate oligomerization reactions comprises at least 10 successive separate oligomerization reactions in which after the end of each reaction said liquid phase and said solids phase are separated from each other and said solids phase is used together with a fresh charge of boron trifluoride and a fresh charge of said oligomerizable 1-olefin in conducting the next oligomerization reaction.

16. A process according to claim 15 wherein said linear 1-olefin is 1-octene and wherein said poly(propylene-co-1-alken-$\overline{\omega}$-ol) polymer is poly(propylene-co-(1-hexen-6-ol).

17. A process according to claim 10 wherein said series of separate oligomerization reactions comprises at least 15 successive separate oligomerization reactions in which after the end of each reaction said liquid phase and said solids phase are separated from each other and said solids phase is used together with a fresh charge of boron trifluoride and a fresh charge of said oligomerizable 1-olefin in conducting the next oligomerization reaction and wherein said poly (propylene-co-1-alken-$\overline{\omega}$-ol) polymer is poly(propylene-co-(1-hexen-6-ol).

* * * * *

UNITED STATES PATENT AND TRADEMARK OFFICE
CERTIFICATE OF CORRECTION

PATENT NO.: 5,811,617

DATED: September 22, 1998

INVENTOR(S): Ronald L. Shubkin, Tze-Chiang Chung, Ruidong Ding

It is certified that error appears in the above-identified patent and that said Letters Patent is hereby corrected as shown below:

Patent reads:

| Col. | Line | |
|---|---|---|
| 5 | 18 | reads "by contacting least"<br>should read --by contacting at least-- |
| 6 | 41 | (Table 1, Column 2) reads "BN in Feed"<br>should read --BBN in Feed-- |
| 7 | 60 | (Table 3, Run No. 9, Reaction Time) reads "i"<br>should read --1-- |
| 10 | 2-3 | reads "polymer is poly(propylene-co-(1-hexen-6-ol)."<br>should read --polymer is poly(propylene-co-1-hexen-6-ol).-- |
| 10 | 16-17 | reads "polymer is poly(propylene-co-(1-hexen-6-ol)."<br>should read --polymer is poly(propylene-co-1-hexen-6-ol).-- |
| 10 | 29 | reads "polymer is poly(propylene-co-(1-hexen-6-ol)."<br>should read --polymer is poly(propylene-co-1-hexen-6-ol).-- |

UNITED STATES PATENT AND TRADEMARK OFFICE
CERTIFICATE OF CORRECTION

PATENT NO.: 5,811,617
DATED: September 22, 1998
INVENTOR(S): Ronald L. Shubkin, Tze-Chiang Chung, Ruidong Ding It is certified that error appears in the above-identified patent and that said Letters Patent is hereby corrected as shown below:

Patent reads:

| Col. | Line | |
|---|---|---|
| 10 | 38-39 | reads "polymer is poly(propylene-co-(1-hexen-6-ol)." should read --polymer is poly(propylene-co-1-hexen-6-ol).-- |

Signed and Sealed this

Nineteenth Day of January, 1999

*Attest:*

*Attesting Officer*

*Acting Commissioner of Patents and Trademarks*